(12) United States Patent
Parker

(10) Patent No.: US 8,016,872 B2
(45) Date of Patent: Sep. 13, 2011

(54) DEPLOYMENT AND DILATION WITH AN EXPANDABLE ROLL SOCK DELIVERY SYSTEM

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/644,784

(22) Filed: Dec. 22, 2009

(65) Prior Publication Data
US 2011/0152760 A1    Jun. 23, 2011

(51) Int. Cl.
A61F 2/06    (2006.01)

(52) U.S. Cl. .................................................. 623/1.11

(58) Field of Classification Search .......... 604/96.01, 604/101.02; 606/194, 198; 623/1.11, 1.12, 623/1.13, 1.15
See application file for complete search history.

(56) References Cited

U.S. PATENT DOCUMENTS

| | | | |
|---|---|---|---|
| 4,732,152 A | 3/1988 | Wallstén et al. | |
| 4,848,343 A | 7/1989 | Wallstén et al. | |
| 4,875,480 A * | 10/1989 | Imbert | 606/194 |
| 5,344,426 A | 9/1994 | Lau et al. | |
| 5,662,703 A | 9/1997 | Yurek et al. | |
| 5,690,644 A | 11/1997 | Yurek et al. | |
| 5,989,280 A | 11/1999 | Euteneuer et al. | |
| 6,004,328 A | 12/1999 | Solar | |
| 6,039,721 A | 3/2000 | Johnson et al. | |
| 6,059,813 A | 5/2000 | Vrba et al. | |
| 6,238,410 B1 | 5/2001 | Vrba et al. | |
| 6,544,278 B1 | 4/2003 | Vrba et al. | |
| 6,547,813 B2 | 4/2003 | Stiger et al. | |
| 6,607,552 B1 * | 8/2003 | Hanson | 623/1.11 |
| 6,702,843 B1 | 3/2004 | Brown et al. | |
| 6,755,855 B2 | 6/2004 | Yurek et al. | |
| 6,774,278 B1 | 8/2004 | Ragheb et al. | |
| 6,866,679 B2 | 3/2005 | Kusleika | |
| 6,918,927 B2 | 7/2005 | Bates et al. | |
| 6,942,682 B2 | 9/2005 | Vrba et al. | |
| 7,201,770 B2 | 4/2007 | Johnson et al. | |
| 7,244,444 B2 | 7/2007 | Bates | |
| 7,303,580 B2 | 12/2007 | Parker | |
| 7,393,358 B2 * | 7/2008 | Malewicz | 623/1.11 |
| 2002/0138127 A1 | 9/2002 | Stiger et al. | |
| 2003/0004561 A1 | 1/2003 | Bigus et al. | |
| 2003/0028243 A1 | 2/2003 | Bates et al. | |
| 2003/0036794 A1 | 2/2003 | Ragheb et al. | |
| 2003/0105508 A1 | 6/2003 | Johnson et al. | |
| 2003/0176910 A1 * | 9/2003 | Vrba et al. | 623/1.11 |

(Continued)

*Primary Examiner* — Nicholas D Lucchesi
*Assistant Examiner* — Aarti B Berdichevsky
(74) *Attorney, Agent, or Firm* — Brinks Hofer Gilson & Lione

(57) ABSTRACT

An expandable roll sock delivery catheter includes an inner tube, an outer tube having a distal outer tube end, and a medical device, such as a self-expanding stent, collapsibly disposed over the inner tube and concentrically oriented between the inner tube and the outer tube. A hollow tube of expandable balloon material extends from the distal outer tube end, the balloon material being substantially disposed in its entirety within a distal end portion of the outer tube. The balloon material is folded back into the outer tube and over the device as a single layer of balloon material connectively linked to the inner tube proximal to the self-expanding device so as to form an expandable roll sock balloon. The roll sock balloon defines an inflation lumen disposed between the outer tube and inner tube, whereby the inflation lumen is configured for expansion of the roll sock balloon following release of the device.

7 Claims, 3 Drawing Sheets

U.S. PATENT DOCUMENTS

| | | |
|---|---|---|
| 2004/0199239 A1 | 10/2004 | Austin et al. |
| 2005/0159803 A1 | 7/2005 | Lad et al. |
| 2005/0159804 A1 | 7/2005 | Lad et al. |
| 2005/0182387 A1 | 8/2005 | Webler |
| 2005/0209676 A1 | 9/2005 | Kusleika |
| 2005/0240254 A1 | 10/2005 | Austin |
| 2006/0009835 A1 | 1/2006 | Osborne et al. |
| 2006/0030923 A1 | 2/2006 | Gunderson |
| 2006/0041302 A1 | 2/2006 | Malewicz |
| 2006/0173422 A1 | 8/2006 | Reydel et al. |
| 2006/0184226 A1 | 8/2006 | Austin |
| 2006/0200221 A1 | 9/2006 | Malewicz |
| 2006/0282152 A1 | 12/2006 | Beyerlein et al. |
| 2007/0073385 A1 | 3/2007 | Schaeffer et al. |
| 2007/0150047 A1 | 6/2007 | Ruane et al. |
| 2007/0196423 A1 | 8/2007 | Ruane et al. |
| 2007/0212394 A1 | 9/2007 | Reyes et al. |
| 2008/0020013 A1 | 1/2008 | Reyes et al. |
| 2008/0027528 A1* | 1/2008 | Jagger et al. .............. 623/1.11 |
| 2010/0168835 A1* | 7/2010 | Dorn ..................... 623/1.11 |

* cited by examiner

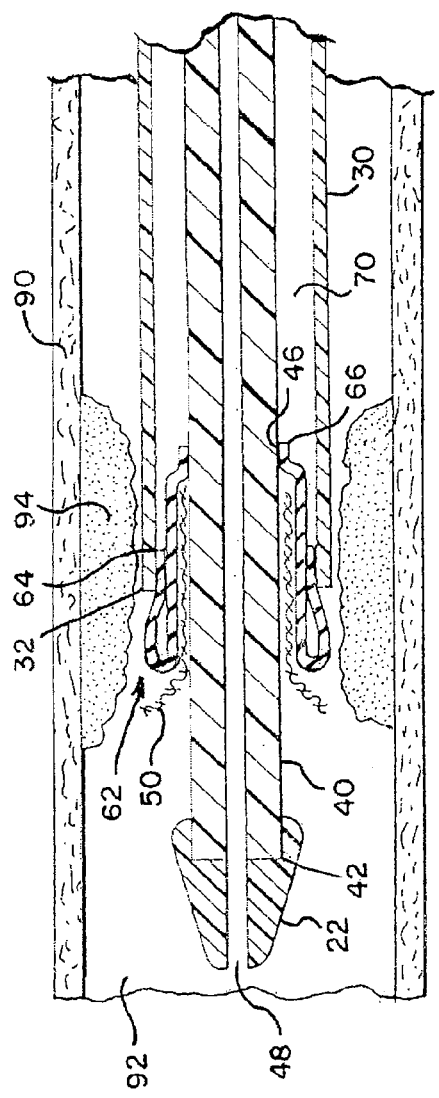
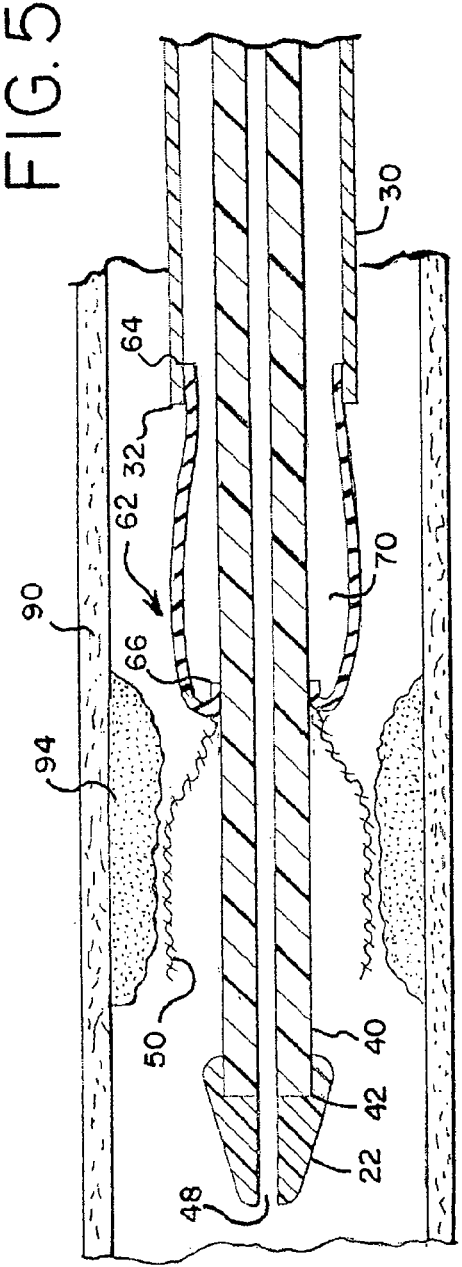

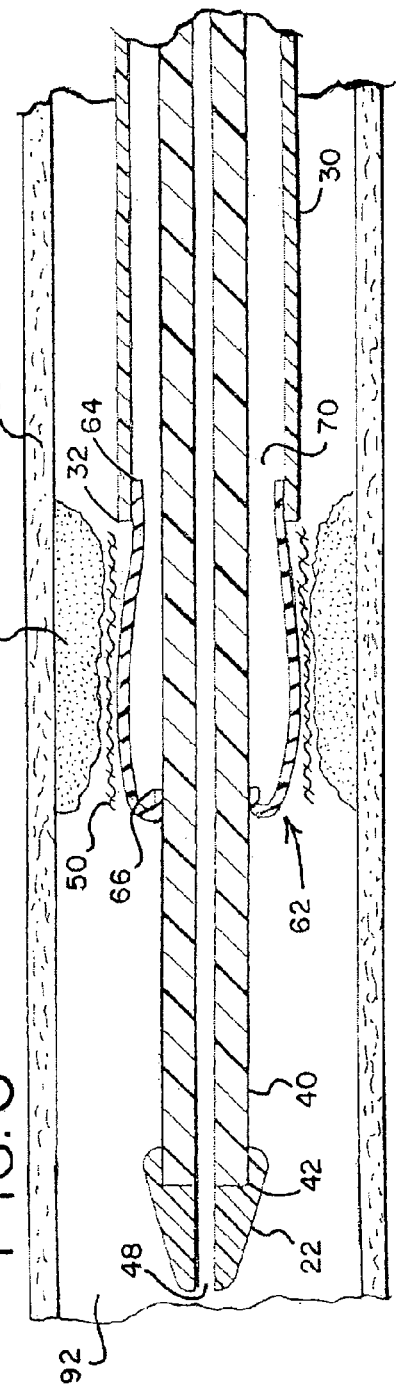
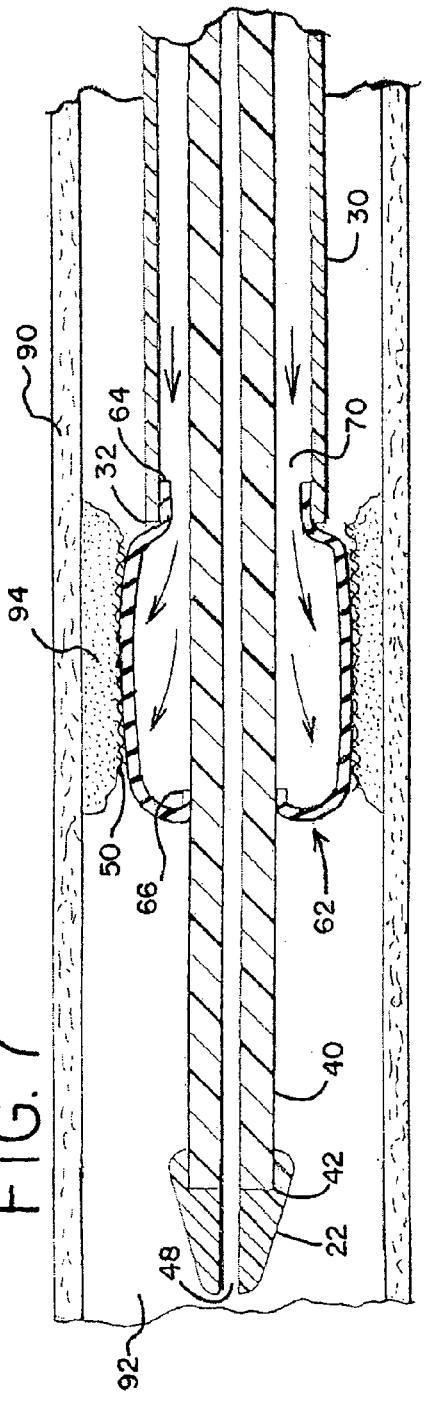

DEPLOYMENT AND DILATION WITH AN EXPANDABLE ROLL SOCK DELIVERY SYSTEM

TECHNICAL FIELD

This invention relates generally to a catheter for delivering medical devices in percutaneous interventional procedures, and more particularly, an endoluminal medical device delivery system and a method for making an endoluminal medical device delivery system for use in angioplasty procedures, stenting procedures, and other device placement procedures and their related devices.

BACKGROUND

Percutaneous interventional angioplasty procedures typically involve guide catheters introduced into the cardiovascular system and advanced through the aorta into a desired coronary artery. Using fluoroscopy, a guide wire is then advanced through the guide catheter and across an artery site to be treated, such as a blockage, lesion, stenosis, or thrombus in an artery lumen. A delivery catheter may then be advanced over the guide wire to deliver a suitable endoluminal medical device, such as a stent, graft, stent-graft, vena cava filter, or other vascular implant. In many cases, a stent is delivered to the treatment site to reinforce body vessels, keep the vessel open and unoccluded, and prevent restenosis. The stent is expanded to a predetermined size, thereby dilating the vessel so as to, for example, radially compress an atherosclerotic plaque in a lesion against the inside of the artery wall. The stent may be a mechanically expandable stent that is expanded using a balloon catheter, for example, or it may be a radially self-expanding stent utilizing resilient or shape memory materials, such as spring steel or nitinol. With respect to a balloon expandable stent, the stent is compressed or crimped about a balloon on the distal end of the catheter. The stent may be covered by an overlying sheath or sleeve to prevent the stent from becoming dislodged from the balloon. With respect to a self-expanding stent, the stent is positioned at a distal catheter end around a core lumen where it is held down (compressed) and covered by an overlying delivery sheath or sleeve. In either case, upon retraction of the sleeve, the stent is able to self-expand and/or be expanded with a balloon. In particular, it is often necessary to remove the stent delivery device and then introduce a separate balloon catheter to "seat" the deployed stent with a balloon.

During the loading and deployment of self-expanding stents, there may be significant frictional forces between the stent surface and the surrounding delivery sheath. These forces may damage the coatings on coated stents, especially longer coated stents, and can create difficulties for sheath retraction and placement. The frictional forces can cause the stent to act like a spring, releasing the stored frictional forces beyond the sheath end and causing the stent to move or "jump" from the desired position and be imprecisely deployed. In addition to the imprecise placement of self-expanding stents, it is often difficult to predict the final stent length in advance of its expansion in the vessel. Further, once a portion of the stent has expanded against the vessel walls, it becomes difficult to adjust its position. Similar problems may occur during the loading and deployment of balloon expandable stents. For example, frictional forces between the protective sheath and the stent may damage any coating on the stent.

U.S. Pat. No. 6,702,843 B1 to Brown et al. discloses a 3-tube stent delivery system, including an outer sheath; an inner sheath; a rollable balloon material folded upon itself and connecting the distal ends of an outer sheath and an inner sheath; and a stent attached around a coaxially positioned inner catheter, constrained by either the inner sheath or the rollable balloon material. An inflation lumen between the outer sheath and the inner sheath may used to dilate a vessel prior to stent deployment. When constrained by the inner sheath, the rollable balloon material may be inflated to dilate a vessel prior to delivery of the stent. When constrained by the rollable balloon material, the balloon may be inflated to seat a stent following its delivery. Brown's 3-tube system limits the size range of stents that may be employed, and depending on its construction, may limit its ability for seating a stent after deployment (when constrained by the inner sheath), or be more prone to inadvertent expansion of the stent (when constrained by the balloon material).

U.S. Pat. No. 7,201,770 B2 to Johnson et al. discloses a stent delivery system, including an outer tube, an inner tube, and a balloon affixed therebetween. An inflation lumen is defined by the space between the inner tube and the outer tube for inflating and deflating the balloon. The balloon is designed to surround and prevent (or constrain) the expansion of a compressed self-expanding stent. The balloon, extending from the distal end of the outer tube is folded back onto itself and affixed to the inner tube, proximal to the stent. When the outer tube is retracted in the proximal direction, the balloon progressively peels back to release the stent. Following release of the stent, the balloon may be positioned within the stent and inflated to fully expand or "tack" the stent in place, as necessary. Johnson characterizes "the unique arrangement of the present invention" in terms of the distal area of the balloon having a novel shape, whereby the distal section of the both the inner and outer balloon portions are tapered inward to protect the leading distal end of the stent and to provide for easier advancement of the catheter system along the desired passage for treatment (col. 2, lines 22-28). However, inasmuch as Johnson relies on the balloon to constrain the stent in a compressed state, Johnson's system risks inadvertent expansion of the stent at an undesired vessel location. Moreover, Johnson's reliance on balloon material to constrain the stent may limit the range and size of stents that can be compressively maintained without significant risk of inadvertent release.

U.S. Pat. Appl. No. 2006/0030923 to Gunderson discloses a stent delivery system comprised an outer tube, an inner tube, and a rollable membrane affixed therebetween. A fluid lumen, defined by the space between the inner tube, the rollable membrane, and the outer tube, is utilized to encourage the rolling action of the membrane and to maintain a gap between the membrane and the outer tube during retraction so as to reduce frictional forces underlying the stent's tendency to push outward against the outer tube. In another embodiment, a secondary fluid lumen extending into the stent receiving region underlying the membrane is utilized to provide a flush path for transporting fluid to the stent receiving region during or prior to delivery of the stent. Gunderson does not suggest an expandable balloon material for use in the membrane, nor does Gunderson suggest inflation of the membrane overlying the fluid lumen to dilate a vessel and/or seat a stent following initial deployment.

In view of the shortcomings and limitations in the prior art, there is a need for a reliable endoluminal medical device delivery system, which addresses the above difficulties by reducing frictional forces hampering stent delivery, by increasing the range of employable self-expanding stents for use, by reducing the risk of inadvertent stent release, and by simplifying the process for setting (or seating) a stent following deployment.

SUMMARY

In one aspect, an expandable roll sock delivery catheter includes an inner tube, an outer tube having a distal outer tube end, and a self-expanding medical device collapsibly disposed over the inner tube and concentrically oriented between the inner tube and the outer tube. A hollow tube of expandable balloon material extends from the distal outer tube end, the balloon material being substantially disposed in its entirety within a distal end portion of the outer tube. The balloon material is folded back into the outer tube and over the self-expanding device as a single layer of balloon material connectively linked to the inner tube proximal to the self-expanding device so as to form an expandable roll sock balloon. The roll sock balloon defines an inflation lumen disposed between the outer tube and inner tube, whereby the inflation lumen is configured for expansion of the roll sock balloon following release of the device.

In one aspect, an expandable roll sock delivery system includes an inner tube, an outer tube, and an expandable medical device collapsibly disposed over the inner tube and concentrically oriented between the inner tube and the outer tube. A first end of a hollow tube of expandable balloon material is attached to a distal portion of the outer tube, and a second end of the hollow tube is attached to the inner tube, such that the balloon material extends over the abluminal surface of the device and is substantially disposed in its entirety within a distal portion of the outer tube. More particularly, the balloon material is attached to the inner and outer tube so as to form an expandable roll sock balloon and an inflation lumen. The inflation lumen is delimited by the space between the outer tube, the roll sock balloon, and the inner tube, and is configured to expand the roll sock balloon following retraction of the outer tube or advancement of the inner tube.

In another embodiment, a method for fabricating an expandable medical device delivery system includes providing an outer tube, an inner tube, an expandable medical device, and a hollow tube of expandable balloon material. The inner tube is co-axially disposed within the outer tube. An expandable medical device is collapsibly disposing on the inner tube. One end of the expandable balloon material is attached to a distal portion of the outer tube; the other end of the balloon material is attached to a portion of the inner tube such that the attached balloon material forms a roll sock balloon and an inflation lumen. The inflation lumen is delimited by the space between the outer tube, the roll sock balloon, and the inner tube and is configured for expanding the roll sock balloon following retraction of the outer tube or advancement of the inner tube. In one delivery system configuration, the roll sock balloon is substantially disposed in its entirety between a distal end portion of the outer tube and the expandable medical device such that a single layer of balloon material substantially covers the entire abluminal side of the medical device on its abluminal side. In a preferred embodiment, the medical device is a self-expanding stent.

In another embodiment, a method for delivering an expandable medical device includes providing an endoluminal medical device delivery system according to the present invention; positioning the distal end of the delivery system in a body lumen proximal to the lesion; retracting the outer tube or extending the inner tube in a manner sufficient for release and radial self-expansion of the medical device; positioning the delivery system so that the roll sock balloon is within a luminal portion of the expanded medical device; and filling the inflation lumen with an amount of inflation fluid sufficient to radially expand the balloon against the medical device, thereby stabilizing the medical device against one or more walls in the surrounding body lumen

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 4 is a side sectional view in which the outer tube of the endoluminal medical device delivery system in FIG. 2 is partially retracted so as to initiate the release of a self-expanding stent.

FIG. 5 is a side sectional view in which the outer tube of the endoluminal medical device delivery system in FIG. 2 has been retracted so as to deploy a majority of a self-expanding stent.

FIG. 6 is a side sectional view in which the roll sock balloon of the endoluminal medical device delivery system in FIG. 2 has been positioned below a stent following its deployment.

FIG. 7 is a side sectional view in which the roll sock balloon in FIG. 6 has been expanded with inflation fluid to reduce vessel narrowing and to set the stent following its deployment.

DETAILED DESCRIPTION

The term "endoluminal medical device" refers to covered and uncovered stents, filters, and any other device that may be implanted in a vascular or bodily lumen or opening in a patient including, for example, a human artery.

The terms "proximal" and "distal" refer to a direction closer to or away from, respectively, an operator (e.g., surgeon, physician, nurse, technician, etc.) who would insert the medical device into a patient, with the tip-end (i.e., distal end) of the device inserted inside a patient's body. Thus, for example, a "proximal portion" would refer to a medical device portion closer to the operator, while a "distal portion" would refer to a medical device portion further away from the operator toward the tip-end of the device.

The term "stent" refers to a device or structure that provides or is configured to provide rigidity, expansion force, or support to a body part, for example, a diseased or otherwise compromised body lumen.

The term "self-expandable" refers to a resilient object, device, or structure having a radially constrained lower diameter configuration when compressed inside a tube or sheath that is capable expanding to form a desired radially-expanded diameter when unconstrained, i.e. released from the radially constraining forces of a tube or sheath, without application of an externally added force.

Figure 1:
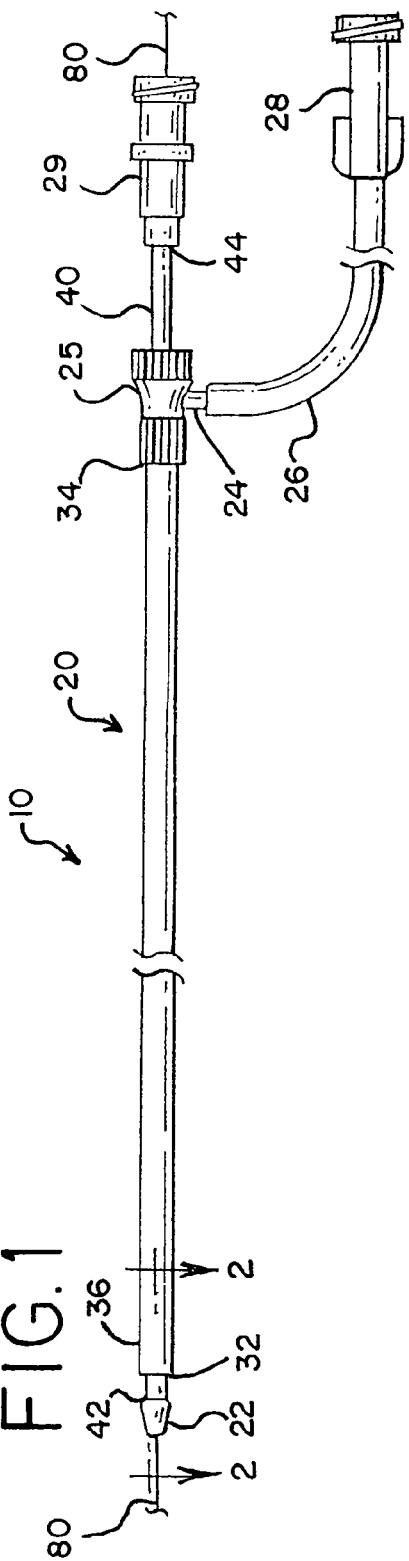
FIG. 1 is a side view of an endoluminal medical device delivery system of the type described in the present invention.

Turning now to the drawings, FIG. 1 depicts an exemplary endoluminal medical device delivery system 10, including a delivery catheter 20. The delivery catheter 20 includes an outer tube 30 defined by a distal end 32, a proximal end 34, and a distal end portion 36. The delivery catheter 20 further includes an inner tube 40 extending longitudinally though an inner passageway of the outer tube 30. The inner tube 40 is connected to a tapered distal tip 22 for accessing and dilating a vascular access site over a guidewire 80, which extends through a lumen of the inner tube 40. The general configuration of the delivery catheter 20 in FIG. 1 is typical of introducer catheters or sheaths known in the art.

In FIG. 1, a connector valve 25, attached about the proximal end 34 of the outer tube 30, typically includes one or more silicone disks (not shown) for preventing the backflow of fluids therethrough. The disks typically include a slit or aperture to allow for passage of the inner tube 40 therethrough. The connector valve 25 also includes a side arm 24 to which a tube 26 and male Luer lock connector 28 may be connected for introducing and/or aspirating fluids through the delivery catheter 20. A guidewire 80 can be inserted in a vessel with an introducer needle using, for example, the well-known percutaneous vascular access Seldinger technique. A male Luer lock connector hub 29 is attached at the proximal inner tube end 44 for connection to syringes and other medical apparatuses.

Figure 3:
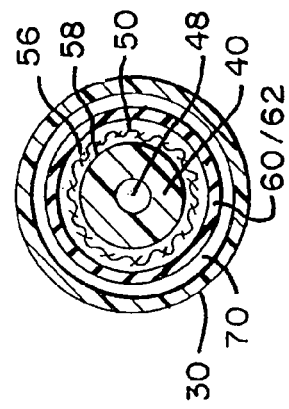
FIG. 3 is a cross-sectional view of the endoluminal medical device delivery system depicted in FIG. 2 and taken along line 3.
Figure 2:
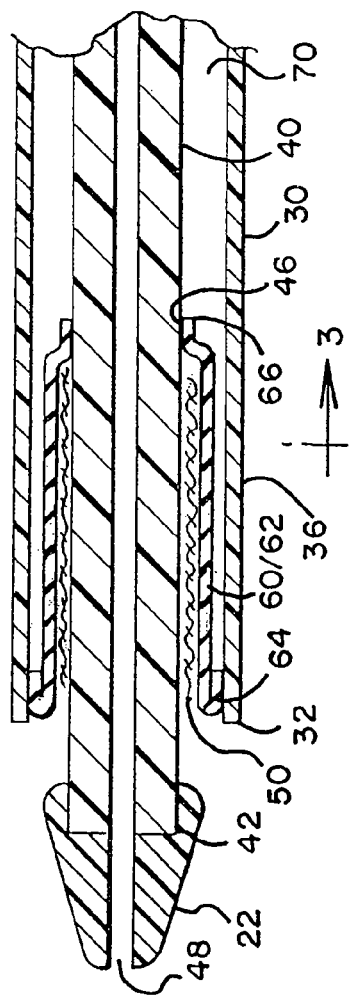
FIG. 2 is a partial side sectional view of an endoluminal medical device delivery system according to one embodiment of the present invention.

FIG. 2 depicts the distal end of a stent delivery catheter 20 housing an endoluminal medical device, which is depicted as a self-expanding stent 50. FIG. 3 depicts a cross-sectional view of the stent delivery catheter 20 depicted in FIG. 2 and taken along line 3. The stent delivery catheter 20 includes an inner tube 40 having a distal end 42 and a proximal end 44, and an outer tube 30 having a distal end 32, a proximal end 34, and a distal end portion 36. The self-expanding stent 50 is collapsibly disposed over the inner tube 40 and concentrically oriented between the inner tube 40 and the outer tube 30, the stent 50 being defined by a distal stent end 52, a proximal stent end 54, an outer abluminal stent side 56, and an inner luminal stent side 58. In FIGS. 1 and 2, the inner tube 40 is further defined by a hollow channel 48 accommodating entry of a guidewire 80 therethrough for purposes of advancing the delivery catheter 20 to a predetermined position in a body lumen or vessel to facilitate delivery of the device 50 by conventional percutaneous delivery means.

A hollow tube of expandable balloon material 60 extends from the distal outer tube end 32 and is substantially disposed in its entirety within the distal portion 36 of the outer tube 30. As shown in FIG. 2, one end 64 of the balloon material 60 is connectively linked to the distal end 32 of the outer tube 30. The other end 66 of the balloon material 60 is folded back into the outer tube 30 and over the inner tube 40, whereby the other balloon material end 66 is connectively linked to the inner tube 40 proximal to the stent 50. Accordingly, a roll sock balloon 62 disposed within the distal portion 36 of the outer tube 36 is formed, whereby the balloon 62 defines an inflation lumen 70 disposed between the outer tube 30 and the inner tube 40. The inflation lumen 70 is configured for expansion of the roll sock balloon 62 following deployment and release of the stent 50. The balloon material may be folded back and connectively linked to more proximal positions of the inner tube 40 to enable balloon expansion over a wider area extending beyond the boundaries of the device 50.

FIG. 2 depicts a tapered tip 22 coupled to the distal end 42 of the inner tube 40. The tip 22 is generally formed from a soft material, such as a soft polymer capable of being bonded to the inner tube 40. Preferably, the tip 22 is tapered and/or rounded to facilitate an atraumatic entry into and through a body lumen. The tip 22 may further include barium sulfate, gold, or other suitable radioapaque and/or MRI contrast agents known to those of skill in the art for fluoroscopic device imaging.

The balloon material 60 may be made from or include one or more surface materials having a low coefficient of friction, so that when positioned between the device 50 and the outer 30 tube, the balloon material 60 is capable of reducing the frictional forces engaging these elements during deployment of the device 50 so as to enhance, for example, retraction of the outer tube 30 and/or advancement of the inner tube 40 to facilitate deployment of a luminally positioned device 50 against a desired vessel wall region.

The inner and outer tubes 40, 30, respectively, are tubular elongate structures that can each be fabricated from multiple materials by conventional co-extrusion processes to form a single layer tube or as a multi-layer tube. Additional layers may be included to provide a desired level of flexibility or stiffness. Accordingly, the inner and outer tubes 40, 30 may be constructed by processes employing single-layer or multiple-layer extrusion; braid coil, stacked coil, or coil-reinforced extrusion; and combinations thereof incorporating a variety of polymeric and/or other suitable materials. In addition, portions of the inner and outer tubes 40, may be tapered in or tapered out as depicted in FIG. 2. The inner and outer tubes 40, 30 may be formed from polymers or polymeric composites. Alternatively, they may be formed from or include non-polymeric materials as well.

Additional polymeric materials or resins used to make the inner and outer tubes 40, 30 include hydrophilic polyurethanes, aromatic polyurethanes, polycarbonate base aliphatic polyurethanes, engineering polyurethane, elastomeric polyamides, block polyamide/ethers, polyether block amide (PEBA), including PEBAX®, silicones, polyether-esters, polyether-ester elastomers, including Arnitel® (DSM Engineering Plastics), nylons, polyesters, polyester elastomers, including Hytrel® (Du Pont), linear low density polyethylenes, such as Rexell®, and combinations thereof.

Any one of the outer and inner tubes may further include a matrix of materials conventionally used in catheters, including reinforcing coils or other supportive materials within, external to or internal to such a matrix. The matrix of materials of materials and/or multilayer construct may be prepared in a variety of catheter configurations for producing a desired level of flexibility or stiffness for a given length of tube. Of course, it will be recognized by those skilled in the art that many different sizes and types of catheters and catheter materials may be employed in conjunction with the present invention, including any of those disclosed in, all of which are expressly incorporated by reference herein.

The delivery system 10 of the present invention may be used to accommodate a variety of radially expandable, including self-expandable luminal devices. Exemplary endoluminal devices include stents, stent grafts, filters, including vena cava filters, valves, occlusion devices, and the like.

Stents, including self-expanding stents can be made of stainless steel, materials with elastic memory properties, such as NITINOL, or any other suitable material. Exemplary self-expanding stents include Z-STENTS™ and ZILVER™ stents, which are available from Cook Incorporated, Bloomington, Ind. USA. Balloon-expandable stents may be made, for example, of stainless steel (typically 316LSS, CoCr, etc.). Hybrid stents may be provided by combining one or more self-expanding stents or stent portions with one or more balloon-expandable stents or stent portions.

A stent may be bare, or it may include a drug coating, such as a coated drug-eluting stent or it may include a covering or graft material, such as stent graft.

Coated drug-eluting stents in the present invention may include a variety of materials for facilitating controlled drug release, including porous polymeric coating layers (US 2007/0150047 A1, 2003/0028243 A1, 2003/0036794 A1, and U.S. Pat. No. 6,774,278 B1), biodegradable elastomeric coating layers (US 2007/0196423 A1), drug coatings (US 2008/0020013 A1, 2007/0212394 A1), porous structures (US 2007/0073385 A1), or surface roughened or textured surfaces (U.S. Pat. No. 6,918,927 B2), the patent disclosures of which are incorporated by reference herein.

Suitable coverings or graft materials for stent grafts may include natural biomaterials, biocompatible polymers, and combinations thereof. Exemplary biocompatible polymers for use in stent grafts include poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments, and combinations thereof, the disclosures of which are disclosed in U.S. Pat. Appl. Nos. 2006/0009835 A1, 2005/0159804 A1, and 2005/0159803 A1, the disclosures of which are incorporated by reference herein. Exemplary biomaterials for use in stent grafts of the present invention include collagen and extracellular matrix materials as described in U.S. Pat. No. 7,244,444 B2, the disclosure of which is incorporated by reference herein.

In a further aspect, a method for fabricating a medical device delivery system 10 includes providing an outer tube 30, an inner tube 40, and an expandable medical device 50. The device 50 is collapsibly disposed around or loaded onto the inner tube. The inner tube 40 and medical device 50 are co-axially disposed within the outer tube and a hollow tube of expandable balloon material 60 is connectively linked between a distal portion 36 of the outer tube 30 and a portion 36 of the inner tube 40 proximal to the device 50. More particularly, a first end 64 of the balloon material 60 is attached to a distal portion 36 or distal end 32 of the outer tube, and a second end 66 of the balloon material is attached to the inner tube 40 at a position 46 proximal to the expandable medical device 50. As a result, a roll sock balloon 62 is formed, the balloon 62 delimiting an inflation lumen 70 between the outer tube 30 and inner tube 40, the inflation lumen 70 being configured for expansion of the roll sock balloon 62 following release of the expandable medical device 50. The balloon material 60 is attached so that a single layer of balloon material 60 is sandwiched between the outer tube and the medical device 50, whereby the balloon material 60 substantial covers the entire abluminal side of the expandable medical device, such that the balloon 62 and the device 50 are substantially disposed in their entirety within a distal portion 36 of the outer tube 30.

In a further aspect, the present invention provides a method for using the above described system 10 to deploy a device 40. More particularly, when deploying a device 50, such as a stent, the guidewire 80 is extended through a vascular or body lumen to a desired device placement site. The delivery catheter 20 is then advanced over and along the guidewire 80 such that the corresponding position of the device 50 is spaced within the desired device placement site. At this point, as shown in FIG. 4, the outer tube 30 may be retracted in a proximal direction relative to the inner tube 40, which causes the roll sock balloon 62 to unfurl from the distal end 32 of the outer tube 30 and to peel away from the abluminal side 56 of the device 50. Alternatively, or in addition, the roll sock balloon 62 may be unfurled by advancing the inner tube 40 in a distal direction relative to the outer tube 30. Once unconstrained by the outer tube 30 or the balloon material 60, radial expansion of a self-expanding device 50 can proceed within the vascular or body lumen 92 at the desired site, such as an atherosclerotic lesion 94 (FIG. 5).

As a further consequence of the unfurling process, the sides of the roll sock balloon 62 will invert relative to their initial configuration prior to the retraction/contraction step(s) (compare FIGS. 2 and 5). From this inverted configuration, inflation fluid can be supplied to the inflation lumen 70 to further expand (or set) the self-expanding device 50. Following positioning of the roll sock balloon 62 within the lumen of the device 50 (FIG. 6) and expansion of the balloon 62 against the device 50 toward the vessel wall 90 to reduce narrowing by the lesion 94 (FIG. 7), the delivery catheter 20 may be removed from the vascular lumen 92.

In view of the device being constrained by the sheath of the outer tube 30 and the configuration of the roll sock balloon 62, the present invention has several benefits: (1) on-site expansion (or setting) of a device following deployment and release without the need for a secondary balloon catheter; (2) roll sock balloon configuration provides an inflation lumen precluding the need for an additional sheath or lumen within a sheath which can increase the width of the delivery catheter and reduce the size limit of the expandable device; (3) design allows for accurate placement and delivery of devices larger in length and/or width; (3) roll sock balloon minimizes difficulties associated with retraction of the outer tube or advancement of the inner tube during deployment of the device; (4) roll sock balloon reduces the frictional forces between surfaces on the device and surfaces on the outer tubes, thereby enhancing more accurate placement of the device; (5) roll sock device helps to better preserve the integrity of a surface coating on a device, such as a coating on a drug-eluting stent.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An expandable roll sock delivery system comprising:
   an inner tube;
   an outer tube;
   an expandable medical device collapsibly disposed over the inner tube and concentrically oriented between the inner tube and the outer tube;
   a hollow tube of expandable balloon material, including a first balloon material end attached to a distal portion of the outer tube, and a second balloon material end attached to the inner tube, the balloon material extending over an abluminal surface of the device and being substantially disposed within a distal portion of the outer tube in an initial configuration;

wherein the balloon material is attached to the inner and outer tube so as to form an expandable roll sock balloon and an inflation lumen, the inflation lumen being delimited by the space between the outer tube, the roll sock balloon, and the inner tube, wherein the inflation lumen is configured for radial expansion of the roll sock balloon following deployment and release of the expandable medical device by retraction of the outer tube or advancement of the inner tube, the balloon material thereby inverting relative to the initial configuration.

2. The delivery system of claim 1, wherein a low friction material is integral to or coated onto the roll sock balloon.

3. The delivery system of claim 2, wherein the low friction material comprises an ultra-high molecular weight polyethylene polymer having a molecular weight between about 1 to about 10 million.

4. The delivery system of claim 2, wherein the low friction material comprises a coefficient of friction of less than about 0.1.

5. The delivery system of claim 1, further comprising an atraumatic tip coupled to the distal end of the delivery system.

6. The delivery system of claim 1, wherein the medical device is a stent.

7. A method for deploying an expandable medical device comprising:
  providing the endoluminal medical device delivery system of claim 1;
  positioning the distal end of the delivery system in a body lumen proximal to a lesion;
  retracting the outer tube or extending the inner tube in a manner sufficient for release and radial self-expansion of the medical device;
  positioning the delivery system so that the inverted roll sock balloon is within a luminal portion of the expanded medical device;
  filling the inflation lumen with an amount of inflation fluid sufficient to radially expand the balloon against the medical device, thereby stabilizing the medical device against one or more walls in the surrounding body lumen.

* * * * *